(12) United States Patent  
Ralph et al.

(10) Patent No.: US 7,922,719 B2
(45) Date of Patent: Apr. 12, 2011

(54) ADJUSTABLE ANGLE PAWL HANDLE FOR SURGICAL INSTRUMENTS

(75) Inventors: James D. Ralph, Bethlehem, PA (US); Thomas N. Troxell, Pottstown, PA (US); Stephen L. Tater, Montville, NJ (US)

(73) Assignee: BioDynamics, LLC, Englewood, NJ (US)

( * ) Notice: Subject to any disclaimer, the term of this patent is extended or adjusted under 35 U.S.C. 154(b) by 1499 days.

(21) Appl. No.: 10/959,571

(22) Filed: Oct. 6, 2004

(65) Prior Publication Data

US 2006/0074428 A1 Apr. 6, 2006

(51) Int. Cl.
*A61B 17/00* (2006.01)
*B25B 23/16* (2006.01)

(52) U.S. Cl. .......... 606/79; 606/84; 606/160; 81/62; 81/177.8

(58) Field of Classification Search .......... 606/84, 606/86 R, 86 A, 86 B, 914–916; 81/60–62, 81/177.8–177.9
See application file for complete search history.

(56) References Cited

U.S. PATENT DOCUMENTS

| | | |
|---|---|---|
| 973,779 A | 10/1910 | Hansen |
| 974,331 A | 11/1910 | Aasen |
| 1,002,215 A | 9/1911 | Bovec |
| 1,068,380 A | 7/1913 | Anderson |
| 1,030,121 A | 12/1913 | Oriol |
| 1,101,381 A | 6/1914 | Anderson et at. |
| 1,173,200 A | 2/1916 | McCraith |
| 1,379,536 A * | 5/1921 | Davies ............ 81/157 |
| 1,387,246 A | 8/1921 | Earle |
| 1,389,200 A * | 8/1921 | Linde ............ 81/177.9 |
| 1,568,442 A * | 1/1926 | Carver ............ 81/177.8 |
| 1,755,486 A * | 4/1930 | Odell ............ 81/177.9 |
| 2,068,207 A * | 1/1937 | Torbert, Jr. ........ 81/177.9 |
| 2,704,479 A * | 3/1955 | Stang ............ 81/177.8 |
| 3,609,864 A * | 10/1971 | Bassett ............ 30/261 |
| 4,100,677 A | 7/1978 | Jeff ............ 30/321 |
| 4,463,632 A | 8/1984 | Parke ............ 81/177.9 |
| 4,711,145 A | 12/1987 | Inoue ............ 81/177.1 |
| 4,802,279 A | 2/1989 | Rowe ............ 30/155 |
| 4,901,608 A | 2/1990 | Shieh ............ 81/177.8 |
| 5,199,335 A | 4/1993 | Arnold et al. ........ 81/177.8 |
| 5,431,671 A | 7/1995 | Nallakrishnan ...... 606/167 |
| 5,536,271 A * | 7/1996 | Daly et al. .......... 606/80 |
| 5,722,168 A | 3/1998 | Huang ............ 30/161 |
| 5,832,791 A * | 11/1998 | Lin ............ 81/62 |
| 5,836,958 A * | 11/1998 | Ralph ............ 606/160 |
| 5,871,204 A * | 2/1999 | Spirer ............ 254/26 R |
| 5,904,689 A | 5/1999 | Jonjic ............ 606/99 |
| 6,000,302 A | 12/1999 | Chiang ............ 81/177.8 |
| 6,186,034 B1 | 2/2001 | Lamons ............ 81/177.9 |
| 6,199,454 B1* | 3/2001 | Bergbower ........ 81/60 |
| 6,216,567 B1 | 4/2001 | Hu ............ 81/177.9 |
| 6,386,075 B1* | 5/2002 | Shiao ............ 81/177.8 |

(Continued)

*Primary Examiner* — Thomas C Barrett
*Assistant Examiner* — Larry E Waggle, Jr.
(74) *Attorney, Agent, or Firm* — Lowenstein Sandler PC

(57) ABSTRACT

A two piece, adjustable angle handle for a surgical instrument, capable of easy adjustment to a number of angles, permitting the handle of the instrument to be grasped with one hand, and the other hand to guide the operating end of the instrument, said handle permanently affixed to an instrument, or capable if attachment to a number of different instruments by means of a firm but releasable fastening to the shaft of the instrument, as with a Hudson fitting; the adjustable angle fastening comprising a radial array of teeth as in a ratchet wheel and a reverse scissor pawl.

16 Claims, 7 Drawing Sheets

U.S. PATENT DOCUMENTS

| | | | |
|---|---|---|---|
| 6,405,621 B1 | 6/2002 | Krivec et al. | 81/177.9 |
| 6,554,864 B2 * | 4/2003 | Ralph et al. | 623/17.11 |
| 6,675,485 B1 | 1/2004 | Shih et al. | 30/321 |
| 6,830,574 B2 * | 12/2004 | Heckele et al. | 606/104 |
| 2003/0061899 A1 | 4/2003 | Liu et al. | |
| 2004/0097947 A1 | 5/2004 | Wolford et al. | |
| 2004/0106928 A1 | 6/2004 | Ek | |
| 2004/0144219 A1 | 7/2004 | Lin | 81/177.8 |
| 2005/0240193 A1 * | 10/2005 | Layne et al. | 606/80 |
| 2006/0074427 A1 * | 4/2006 | Lieberman | 606/84 |

* cited by examiner

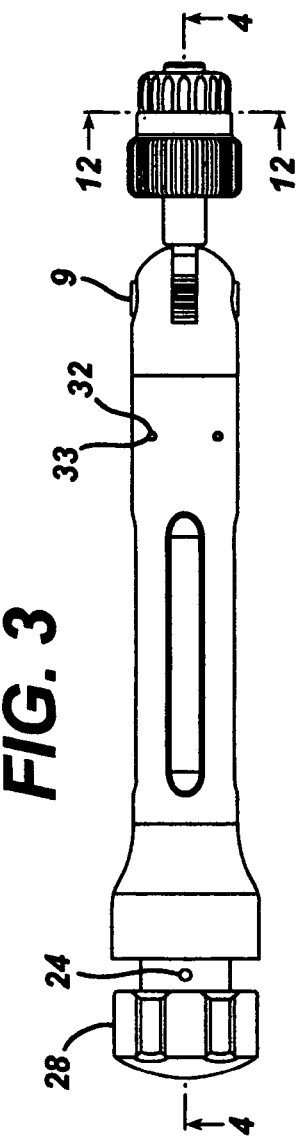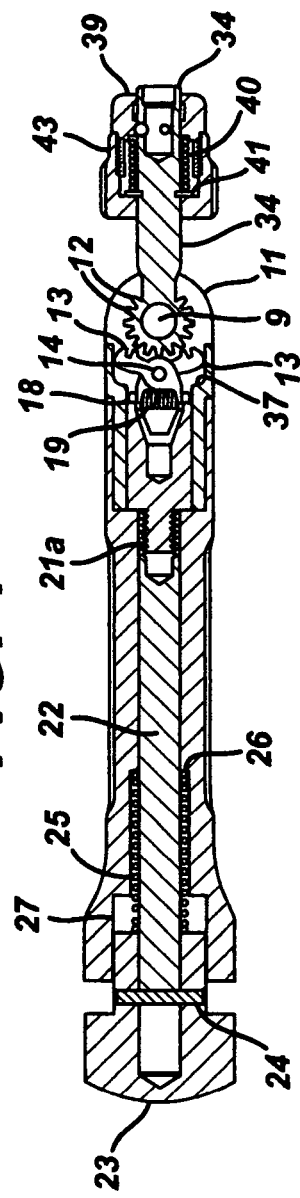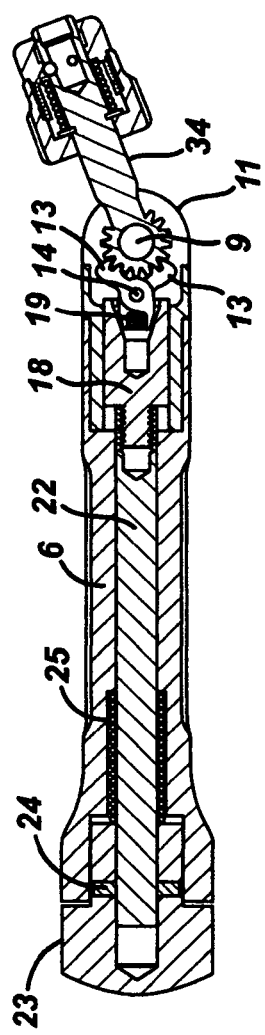

ADJUSTABLE ANGLE PAWL HANDLE FOR SURGICAL INSTRUMENTS

FIELD OF THE INVENTION

The present invention relates to surgical instruments and particularly to orthopedic surgical instruments for cutting and scraping bone.

BACKGROUND OF THE INVENTION

When using certain orthopedic surgical instruments, such as curettes and chisels, for the removal of osteophytes, the surgeon must apply a great a degree of force. Often, this requires the surgeon to use a two handed grip on the straight handle of the instrument. Depending on the angle with which the force may be applied, the two-handed grip may also limit the amount of force that may be applied, and make it difficult to control the operating end of the instrument. In particular, when cleaning out the long bone prior to a hip implant, the surgeon generally grasps the handle of the straight curette with both hands, and moves it in an up-and-down direction. Being able to adjust the angle of the handle with respect to the shaft of the curette will give the surgeon a better angle for cutting, and a better grip, and enable the surgeon to apply force at the handle using only one hand, and use his/her other hand to guide the operating end of the instrument.

SUMMARY OF THE INVENTION

It is an object of the present invention to provide an easily adjustable, angled handle for surgical instruments, which provides a better grip for the surgeon, for better overall control and manipulation of the instrument.

It is an object of the invention to provide an adjustable angle handle for a surgical instrument which permits the surgeon to control the instrument with one hand, and guide the operating end of the instrument with the other hand.

It is an object of the invention to provide and adjustable angle handle adaptable for use with a number of instruments, to thereby reduce the cost of adjustable angled handles for surgical instruments.

It is an object of the invention to provide an angled handle for a surgical instrument that may be easily adapted for use by both right and left handed surgeons.

It is an object of the invention to provide a multiple user adjustable angle handle for surgical instruments, to reduce the number of handles needed in inventory, and reduce the cost of adjustable angle handles for surgical instruments.

It is another object of the invention to increase the ease of use of various surgical instruments, by permitting the one-handed wielding of the handle; permitting the surgeon a better angle of approach with the instrument. In particular, use in the adjustable angle handle permits easier use of the instrument in the surgical environment regardless of available operating space requirements.

These objects, as well as other objects which will become apparent from the discussion that follows, are achieved, in accordance with the present invention, which comprises and adjustable angle handle for a surgical instrument, or an adjustable angle handle for use with a number of instruments, by means of a multiple instrument retainer shaft and instrument connector. The adjustable angle handle has a hand gripping portion rotatably connected to the instrument, or the multiple instrument retainer shaft, and means for fixing the angle of rotation, fixing the angle of the hand gripping portion to the instrument shaft. The rotatable connection is achieved by a transverse pin at the distal end of the hand gripping portion, which passes through an instrument shaft connector, comprising a transverse bore at the proximal end of the instrument shaft, or the multiple instrument retainer shaft. The pin may be directly mounted to the hand gripping portion of the handle, or, for ease of assembly, mounted to a housing fixedly attached to the distal end of the hand gripping portion. A plurality of teeth extend approximately radially from about the transverse bore.

To fix the angle of the handle, a reverse scissor pawl is attached to the hand gripping portion, proximal to the fixed pin, transverse bore and teeth. The reverse scissor pawl has two interlocking arms, rotatably attached about a pawl pin, attached transversely to the hand gripping portion, The distal ends of the pawl arms form locking jaws, which close when the proximal end of the pawl arms are closed.

Proximal to the scissor pawl is a pawl cam, which is attached to a shaft extending through the hand gripping portion to a locking knob. The distal end of the pawl cam comprises the leading edges of the pawl movement surface. The proximal ends of the arms of the pawl are contained within the leading edges of the cam. When the knob is pushed forward, the cam moves forward, and the movement surface of the cam brings the proximal end of the pawl arms together, and brings the locking jaws of the scissor together, engaging the teeth of the shaft connector. A compression spring is mounted between the proximal ends of the arms of the pawl, applying an expansion force to open the proximal ends and the locking jaws of the pawl.

The pawl cam may be locked in the forward position, with the pawl locking jaws engaging the teeth of the shaft connector, by means of at least one locking pin, extending from the hand gripping portion into at least one groove in the knob, having at least one radial portion. Preferably, the transverse and radial grooves meet in an L-shape. Also, in the preferred construction of the handle, the hand gripping portion comprises a retainer housing from which the fixed pin, establishing rotation between the handle and the shaft, is attached. Most preferably, the retainer housing comprises two half housings, for containing the shaft connector and the pin, therethrough. The housing may have a flange, for insertion into the distal end of the hand gripping portion; and retainer openings in the flange, which mate with openings in the hand gripping portion, to receive handle retaining pins.

The ability to adjust the angle of the handle with respect to the instrument shaft permits the surgeon tremendous ease of use, a far greater degree of control of the instrument, and enhanced access to surgical sites; each of which will improve the opportunity for surgical success, and may lead to the development of new surgical procedures. The angle of the handle may be adjusted by the surgical nurse or the surgeon. The angle may be readjusted mid-procedure by rotating the locking knob, and releasing the pressure on the knob, and permitting the compression spring between the proximal end of the arms of the pawl to separate the ends, and the locking jaws, releasing the shaft connector. The instrument may then be adjusted to a different angle with respect to the handle and the knob pushed forward to lock the jaws of the pawl to different set of teeth on the shaft connector. This may be easily accomplished with the two hands of a single user, without having to put the instrument down, or take it apart.

For a full understanding of the present invention, reference should now be made to the following detailed description of the preferred embodiments of the invention as illustrated in the accompanying drawings.

BRIEF DESCRIPTION OF THE DRAWINGS

FIG. 3 is a side view of the adjustable angle handle of FIG. 2.

FIG. 4 is a cross-sectional view of the adjustable angle handle of FIG. 3, viewed along lines 4-4.

FIG. 5 is a cross-sectional view of the adjustable angle handle of FIG. 3, with the knob pushed toward the instrument, and the pawl engaging the teeth, 12.

DESCRIPTION OF THE PREFERRED EMBODIMENTS

Figure 1:
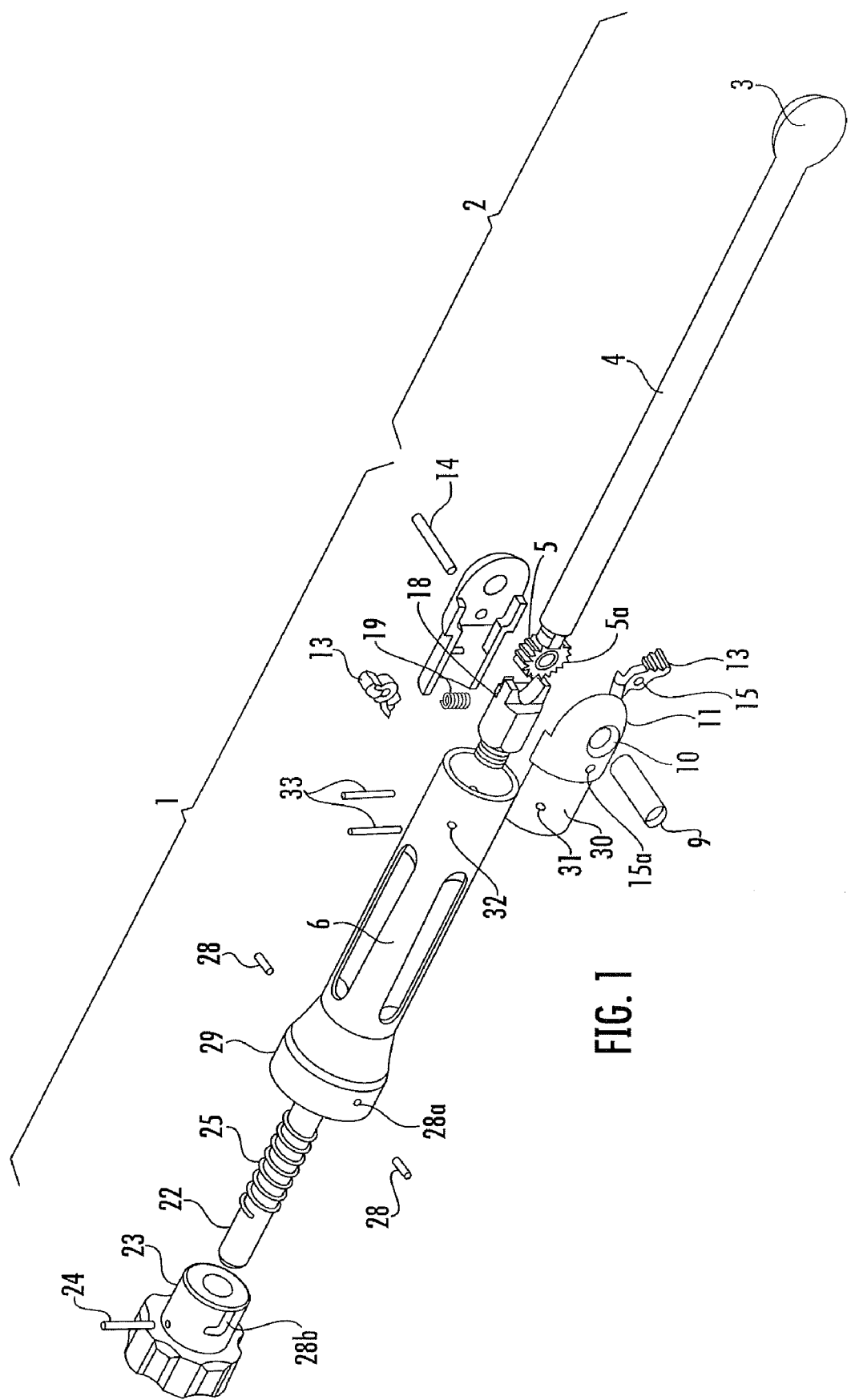
FIG. 1 is an exploded perspective view of a surgical instrument with an adjustable angle handle with locking pawl according to the present invention.

The new handles are especially advantageous for use with orthopedic surgical instruments, such as curettes, chisels, taps and probes; and most especially, with larger chisels. They may also be used with drills. New applications will be found as a result of the remarkable ease of use of the handle.

The preferred embodiments of the present invention will now be described with reference to FIGS. 1-9 of the drawings. Identical elements in the various figures are designated with the same reference numerals.

FIG. 1 illustrates an exploded perspective view of a surgical instrument with an adjustable angle handle with locking reverse scissor pawl, according to the present invention. The handle is illustrated generally at 1, and the instrument at 2. The instrument has an operating end, 3, a shaft, 4, and a shaft connecting portion, 5. The shaft connecting portion, 5, comprises a transverse bore 5a, perpendicular to the length of the shaft of the instrument, and a plurality of paralleled teeth, 12, arranged in a radial pattern about the bore, 5a, in the pattern of a ratchet wheel. The handle has a hand gripping portion, 6, with a fixed retaining pin, 9, attached at the distal end, perpendicular to the length of the handle. When fully assembled, the fixed pin, 9, extends through the transverse bore, 5a, of the shaft connecting portion, 5, of the instrument shaft and attaches to the handle.

In the embodiment shown, a housing, 10, is used to attach the fixed retaining pin to the hand gripping portion of the handle For ease of assembly, the housing may comprise two half retainer housings, 11, with two opposed openings, 10, for receiving the fixed pin, 9. Within the hand gripping portion of the handle is a reverse scissor pawl, 13, for engaging and releasing the teeth, 12, to adjust the angle of the hand gripping portion with respect to the instrument shaft. The reverse scissor pawl comprises two crossed, interlocking pawls arms, rotatably mounted on a pin, 14, through openings 15 in the pawl arms, which is illustrated in FIG. 4. The pin 14 then extends through opposed openings 15a in the half retainer housings, securing it to the hand gripping portion.

Figure 6A:
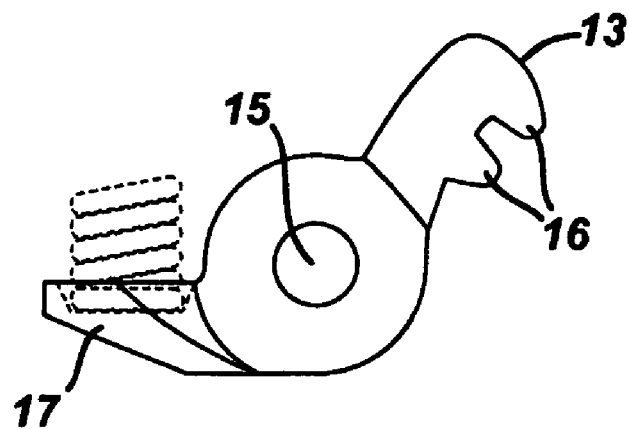
FIG. 6A is a left side view of the right arm of the reverse scissor pawl.
Figure 6B:
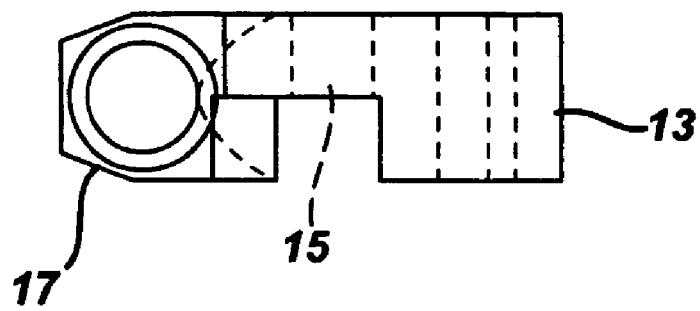
FIG. 6B is a top view, of the right arm of the reverse scissor pawl of FIG. 6A.

As shown in FIG. 6A, each arm of the scissor pawl has a locking jaw, 16, which engage the teeth, 12, of the ratchet wheel structure of the instrument shaft connecting portion. The proximal end, 17, of each arm of the pawl has a recess, shown by the dotted line in FIG. 6A, for receiving the spring, 19, which applies an expansion force to separating the proximal ends, and thereby the jaws, of the reverse scissor pawl.

Figure 7:
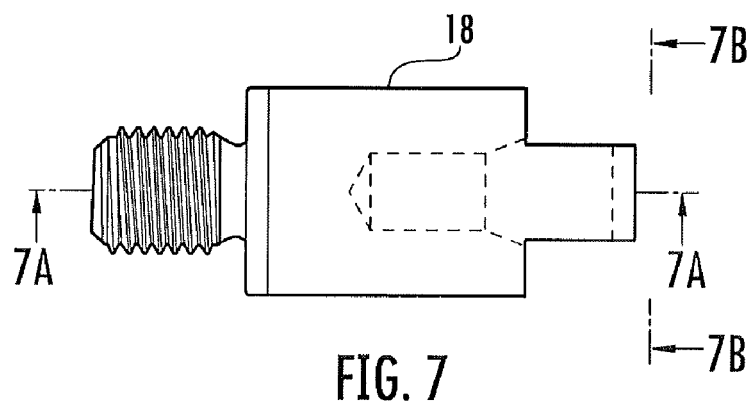
FIG. 7 is a top view of the pawl cam.
Figure 7A:
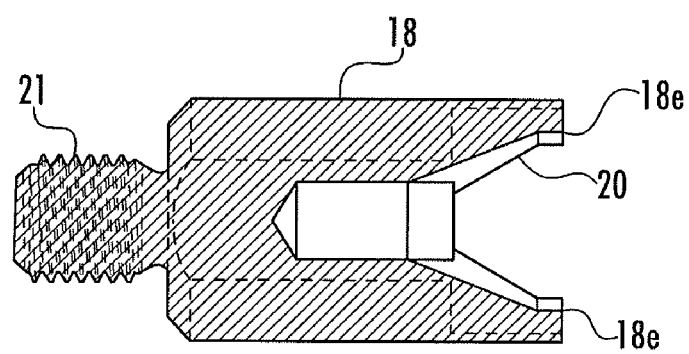
FIG. 7A is a cross-sectional view of the pawl cam of FIG. 7, taken along lines 7A-7A.
Figure 7B:
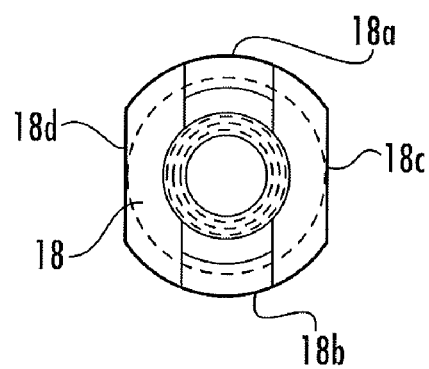
FIG. 7B is a cross-sectional view of the pawl cam of FIG. 7, taken along lines 7B-7B.

As may best be seen in FIGS. 4, 5 and 7A, the ends of the arms of the reverse scissor pawl are contained within the leading edges, 18e, of the pawl cam, 18. When the pawl cam is moved forward, the proximal ends of the arms of the pawl are moved by the working surface, 20, of the pawl cam, as shown in FIG. 7A. This movement presses the proximal ends of the arms together, compressing the spring, 19, and closing the locking jaws of the pawl. The pawl cam is attached, i.e. by a threaded attachment, 21, to the threaded portion 21a of central shaft, 22, of the handle which extends through a central bore running the length of the hand gripping portion of the handle. As may be seen in FIGS. 7, and 7B, the pawl cam does not have a round cross section. Both the top and bottom surfaces, 18a & 18b, of the pawl cam are rounded to move easily along the central bore of the handle, while the sides, 18c & 18d, are trimmed, for placement of the handle retaining pins, as explained below.

Referring to FIGS. 1-5, central shaft extends through the bore of the handle, and beyond the proximal end off the hand gripping portion. An angle adjustment locking knob, 23, is attached to the proximal end of the shaft by knob retaining pin, 24. A compression spring, 25, is mounted on the shaft between the knob and the shoulder, 26 in the central bore of the handle. A knob receiving bore, 27, is provided at the proximal end of the hand gripping portion and permits the knob to be pushed into the hand gripping portion, pushing the pawl cam over the proximal ends of the scissor pawl, compressing the spring between the proximal ends of the arms of the reverse scissor pawl, and closing the locking jaws of the reverse scissor pawl onto the teeth 12 of the instrument shaft connector.

Locking pins, 28, extend through openings 28a at the enlarged proximal end, 29, of the hand gripping portion of the handle, and into the central bore, to engage locking channel 28b, having a radial locking section and a lengthwise section to accommodate forward and reverse motion of the knob and shaft, locking and unlocking the jaws of the pawl. In the embodiment shown in FIG. 1, there are two locking pins and two L-shaped groves (one unshown), however the present invention is not limited to an L-shape groove, or any particular number of locking pins.

Mating flanges, 30, of the half retainer housings have retaining openings at 31 for handle retaining pins, 33. When the half retainer housings are brought together and the flanges placed through the distal end of the hand gripping portion, these retaining openings, 31 aligned with openings, 32 in the distal end of the hand gripping portion of the handle. Two handle retaining pins, 33 extend through the handle from top to bottom, on either side of the pawl cam.

Figure 2:
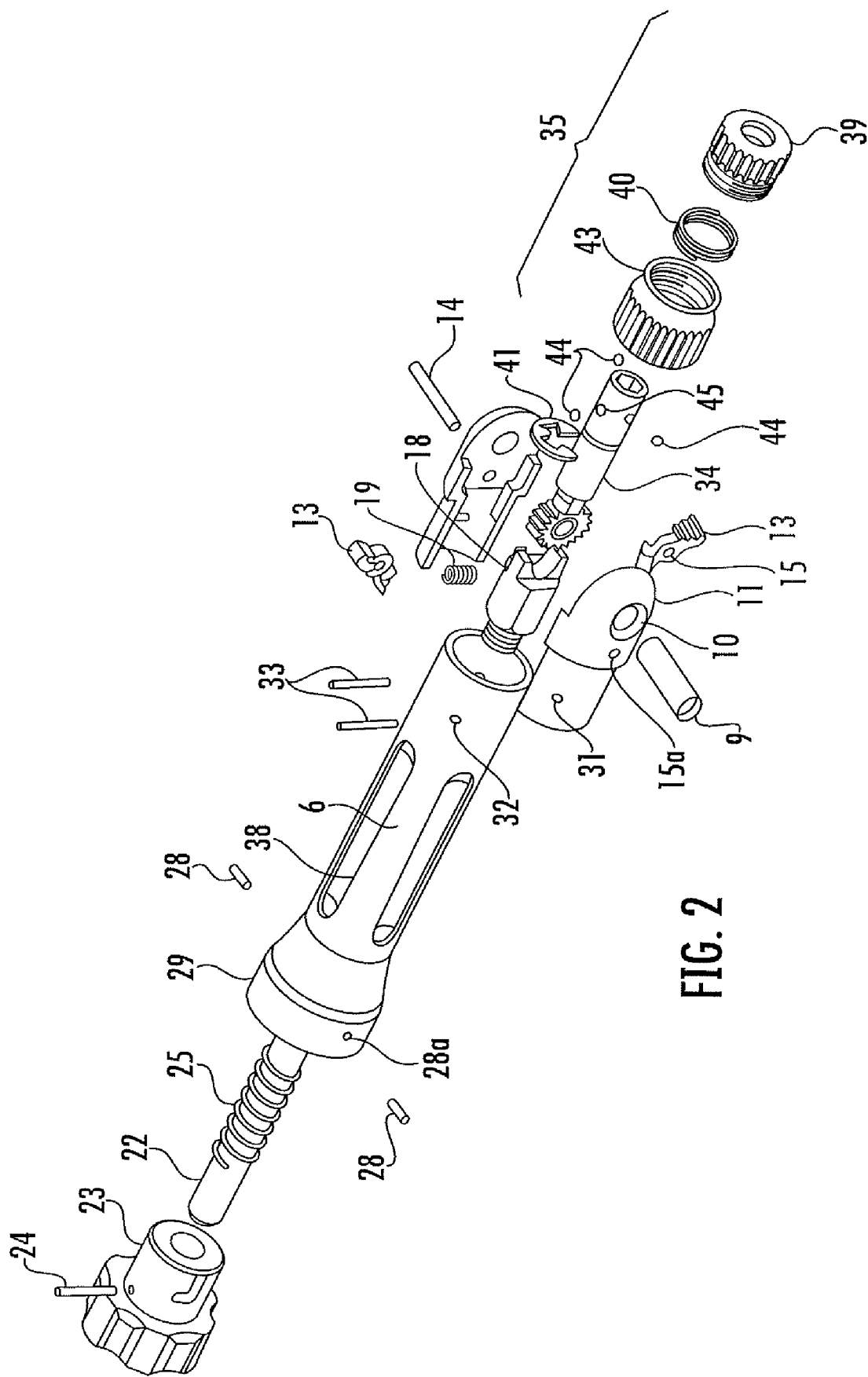
FIG. 2 is an exploded perspective view of an adjustable angle handle with locking pawl for use with one or more surgical instruments, according to the present invention.
Figure 9:
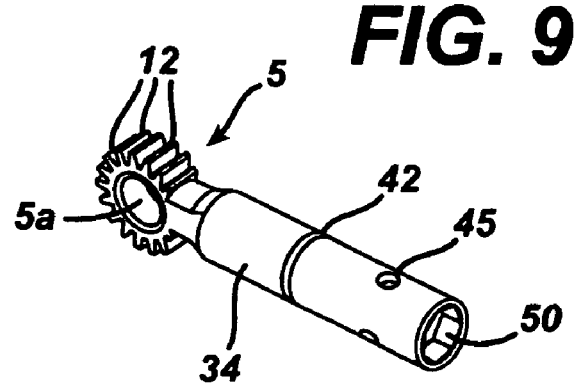
FIG. 9 is a top perspective view of the instrument loader shaft.

FIG. 2 is an exploded perspective view of an adjustable angle handle, according to the present invention, which may be used with a number of different surgical instruments. In this embodiment of the invention, the shaft of the instrument has been replaced by an instrument retainer shaft, 34, an enlarged perspective view of which is shown in FIG. 9. At the distal end of the instrument retainer shaft is an instrument connector, 35, comprising a quick connect, and/or quick disconnect assembly, as is known in the art. In this embodiment the connector is a traditional Hudson fitting, however other known fittings, such as, i.e., a taper lock, agent three to four finger collet combo or a set screw cobble may be used to create the instrument connector.

Figure 8A:
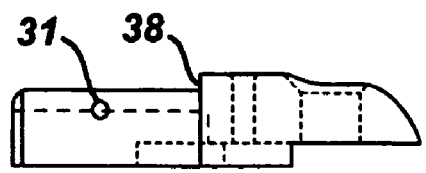
FIG. 8A is a top view of a half retainer housing.
Figure 8B:
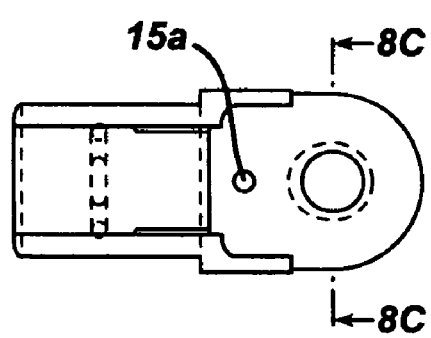
FIG. 8B is a side view of a half retainer housing.
Figure 8C:
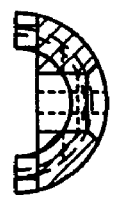
FIG. 8C is a cross-sectional view of the half housing of FIG. 8B taken along lines 8C-8C.

FIG. 3 illustrates a top view of the handle shown in FIG. 2. FIG. 4 is a cross-sectional view of the handle of FIG. 3, taken along lines 4-4. As may be easily seen in FIG. 4, the half retainer housings, 11, illustrated more fully in FIGS. 8A-8C, are identical. Each half retainer housing portion had an opening, 10, for the fixed retainer pin, 9. Prior to assembling the housing, the retaining pin, 9, is disposed through the transverse bore 5a of the instrument retainer shaft. Then, the two half retainer housings are assembled about the ratchet wheel structure of the shaft connector, and pin, 9 disposed through openings 10 in the half retainer housings. This aligns the flanges 30, and the flange retainer openings, 31, of the housing, which may then be inserted into the distal end of the hand gripping portion. As shown, the flanges abut the rounded shoulder, bore, 37, and the shoulder, 38 of the flanges abuts the end surface of the distal end of the hand gripping portion.

The operation of the adjustable angle handle is best understood in relation to FIGS. 4 and 5. The adjustable 20 angle connection is achieved by the transverse bore, 5a, in the shaft connector and fixed pin, 9, attached transversely to the distal end of the hand gripping portion. Fixing the angle is achieved by the reverse scissor pawl, 13, comprising crossed locking pawl arms rotatably mounted on pawl pin, 14 disposed through the aligned openings 15 in the pawls as shown in cross-section in FIG. 4. The pawl pin further extends through openings 15a in the housing, to secure to locking pawls at the distal end of the hand gripping portion. The proximal ends, 17 of the interlocking pawls are disposed within the pawl cam, 18, and the pawl cam is attached to the central shaft extending through the hand gripping portion to the angle adjustment locking knob. This mechanism is constructed and functions similarly to the embodiment described in relation to FIG. 1, with forward movement of the pawl cam compressing the spring between the proximal ends of the arms of the scissor pawl as the proximal ends of the arms of the scissor pawl move along the working surface of the pawl cam, closing the proximal ends of the arms of the pawl, causing the locking jaws 16 of the pawl to engage the teeth 12 of the shaft connector.

As illustrated in FIG. 2, the hand gripping portion of the handle of the present invention may also be provided with a molded region to create a gripping surface, 38, which allows the surgeon to bore easily grasp and manipulate the handle with one hand. The hand gripping portion may also be provided with an enlarged end, 29, to insure the surgeons hand does not slip from the handle especially when using a one-handed grip.

Figure 10:
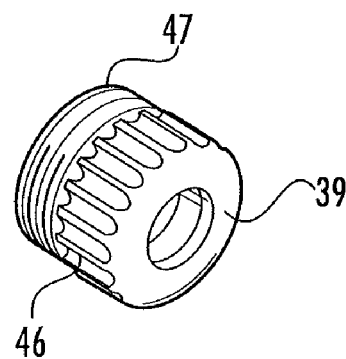
FIG. 10 is a perspective view of the instrument retaining cap
Figure 11:
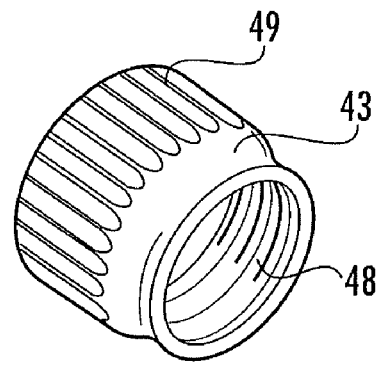
FIG. 11 is a perspective view of the retainer release housing.
Figure 12:
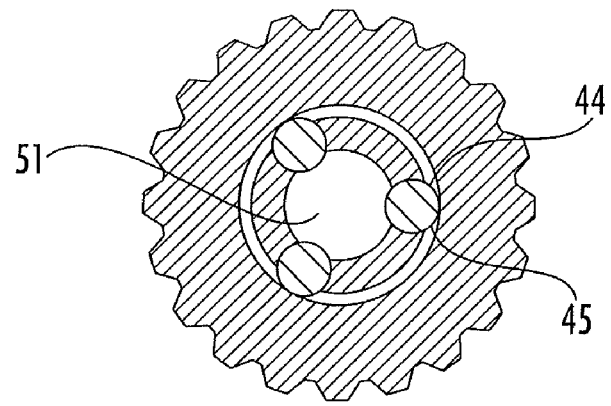
FIG. 12 is a cross-sectional view of FIG. 3, taken along line 12-12.

The instrument connector, 35, on the instrument retainer shaft, 34, comprises an instrument retaining cap, 39, a compression spring, 40, and an E-ring, 41, in transverse groove, 42, of the instrument retainer shaft, a retainer release housing, 43, and instrument retaining balls (at least 3), 44, staked into openings 45, (at least three) in instrument retainer shaft 34. Instrument retaining cap, 39 is illustrated more fully in FIG. 10, showing its outer knurled surface, 46, and external threads, 47. The retainer release housing, 43 is more fully illustrated in FIG. 11, showing its internal threads, 48 and outer knurled surface 49. FIG. 12 illustrates the openings 45 and instrument retainer balls, 44, in a cross-section of FIG. 3.

As shown in FIG. 4, when assembled, the instrument retainer shaft, 34, and the retainer release housing, 43, are mounted on the instrument retainer shaft, the E-ring 41 is then disposed within the groove, 42 of the instrument retainer shaft, the compression spring, 40 is placed about the instrument retainer shaft the instrument retaining top disposed on the instrument retainer shaft, 34 and the 20 exterior threads, 47 of the instrument retaining cap secured to the internal threads, 48 of the retainer release housing, 43.

To secure an instrument in the instrument retainer shaft, the user pulls back on the retainer release housing, 43, and inserts the instrument shaft or connector into guide 50 to align the instrument in the instrument retaining chamber, 51. The guide, 50, illustrated in FIG. 9, is a hexagonal guide, however, it is only necessary that the guide cooperate with the surface(s) of the instrument to orient the instrument in the chamber, such that a tight grip is achieved with a particular instrument connector. Upon release of the retainer release housing, 43, the compression spring pushes the instrument retaining cap forward and drives the instrument retaining balls down into the groove on the instrument, as may be more fully seen in FIG. 12, firmly securing the instrument to the handle.

If desired, the instrument shaft, or connector, may have a shoulder which mates with the guide. When the instrument shaft or connector is in the chamber, the instrument retaining cap, 39 is screwed into the retainer release housing, 43, to firmly grip the shaft of the instrument. To release the instrument, retainer release housing, 43 is rotated with respect to the instrument retaining cap, 39, releasing the threads, and the compression spring, 40, pushes the instrument retaining cap forward to release the pressure on the shaft of the instrument.

There has thus been shown and described a novel adjustable angle handle with a locking reverse scissor pawl for surgical instruments which fulfills all the objects and advantages sought therefore. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

The invention claimed is:

1. A surgical instrument assembly having an adjustable handle comprising,
   (a) an instrument retainer shaft having a distal end and a proximal end wherein the distal end has an operating end of a surgical instrument disposed thereon and the proximal end comprises a shaft connecting portion having a transverse bore, and a plurality of teeth approximately radially arrayed from the bore, and;
   (b) a hand gripping portion having a proximal end and a distal end, and a fixed pin attached at the distal end of the hand gripping portion transversely to the length of the hand gripping portion and disposed through the transverse bore of the proximal end of the instrument retainer shaft;
   (c) a reverse scissor pawl attached to a transverse pawl pin fixed at the distal end of the hand gripping portion, said pawl comprising interlocking scissored arms rotateably mounted on said pawl pin, each arm comprising a proximal end and a distal end and having a locking jaw at its distal end, said pawl pin attached to the hand gripping portion proximal to the fixed pin, such that the locking jaws engage the teeth when the scissor pawl is closed;

(d) means for opening and closing the jaws of the scissor pawl to adjust the angle of the handle with respect to the instrument retainer shaft, the means for opening the scissor pawl comprising a transverse compression spring disposed between the proximal end of the arms of the scissor pawl, the spring applying an expansion force between the proximal ends of the arms of the scissor pawl to open the scissor pawl, and the means for closing the scissor pawl comprising a pawl cam, proximal to the pawl, and comprising leading edges adjacent a movement surface, said leading edges extending about the proximal ends of the arms of the pawl, said cam mounted to a cam shaft extending through the hand gripping portion and extending from the proximal end of the hand gripping portion to a knob, such that a forward motion of the knob and cam shaft closes the scissor pawl; and (e) means for locking the cam shaft in the forward position and locking the pawl jaws in engagement with the teeth, comprising at least one locking pin extending from the hand gripping portion into a groove in the knob having a radial portion.

2. A surgical instrument assembly as in claim 1, wherein the means for locking comprises a second locking pin mounted on the hand gripping portion and extending into the bore of the hand gripping portion and extending into the transverse bore of the hand gripping portion, and a transverse groove in the knob for receiving the second locking pin, and a lateral groove in the knob to accommodate the forward and reverse motion of the cam shaft, knob and locking pin, to open and close the pawl.

3. A surgical instrument assembly as in claim 1, further comprising a housing, wherein the housing comprises mating right and left half retainer housings, assembled about and containing the reverse scissor pawl on the pin and the plurality of teeth approximately radially arranged from the bore.

4. A surgical instrument assembly as in claim 3, wherein each half retainer housing comprises a half-dome shape, with a recessed flange attached to the base thereof, each said recessed flange being disposed within the distal end of the hand gripping portion and fixedly retained therein.

5. A surgical instrument assembly as in claim 4, wherein the recessed flanges of the half retainer housing portions are fixedly retained therein by at least one dowel pin disposed through holes in the distal end of the hand gripping portion, and mating retaining openings in the flanges.

6. A surgical instrument assembly as in claim 5, wherein each recessed flange further comprises a shoulder adjacent the half-dome, and the distal end of the hand gripping portion comprises an end surface mating to a recessed flange shoulder, to stabilize the attachment of the hand gripping portion to the shaft connecting portion of the instrument.

7. A surgical instrument assembly as in claim 6, wherein the hand gripping portion has an enlarged proximal end and the surface of the hand gripping portion comprises molded regions creating a gripping surface.

8. A surgical instrument assembly having an adjustable handle, comprising, (a) an instrument retainer shaft having a distal end and a proximal end, wherein the distal end has a surgical instrument connector and the proximal end comprises a shaft connecting portion having a transverse bore, and a plurality of teeth approximately radially arrayed from the bore;

(b) a hand gripping portion, having a proximal end, and a distal end, and a fixed pin attached at the distal end of the hand gripping portion, transversely to the length of the hand gripping portion and disposed through the transverse bore of the proximal end of the instrument retainer shaft;

(c) a reverse scissor pawl attached to a transverse pawl pin fixed at the distal end of the hand gripping portion, said pawl comprising interlocking scissored arms rotateably mounted on said pawl pin, each arm comprising a proximal end and a distal end and having a locking jaw at its distal end, said pawl pin attached to the hand gripping portion proximal to the fixed pin, such that the locking jaws engage the teeth when the scissor pawl is closed;

(d) means for opening and closing the jaws of the scissor pawl to adjust the angle of the handle with respect to the instrument retainer shaft, the means for opening the scissor pawl comprising a transverse compression spring disposed between the proximal end of the arms of the scissor pawl, the spring applying an expansion force between the proximal ends of the arms of the scissor pawl to open the scissor pawl, and the means for closing the scissor pawl comprising a pawl cam, proximal to the pawl, and comprising leading edges adjacent a movement surface, said leading edges extending about the proximal ends of the arms of the pawl, said cam mounted to a cam shaft extending through the hand gripping portion and extending from the proximal end of the hand gripping portion to a knob, such that a forward motion of the knob and cam shaft closes the scissor pawl;

(e) means for locking the cam shaft in the forward position and locking the pawl jaws in engagement with the teeth, comprising at least one locking pin extending from the hand gripping portion into a groove in the knob having a radial portion; and a plurality of surgical instruments configured to be interchangeably attached to the surgical instrument connector.

9. A surgical instrument assembly as in claim 8, wherein the means for locking comprises a second locking pin mounted on the hand gripping portion and extending into the transverse bore of the hand gripping portion, and a transverse groove in the knob for receiving the second locking pin, and a lateral groove in the knob to accommodate the forward and reverse motion of the cam shaft, knob and locking pin, to open and close the pawl.

10. A surgical instrument assembly as in claim 8, further comprising a housing, wherein the housing comprises mating right and left, half retainer housings, assembled about, and containing the reverse scissor pawl on the pin, and the plurality of teeth approximately radially arranged from the bore.

11. A surgical instrument assembly as in claim 10, wherein each half retainer housing comprises a half-dome shape, with a recessed flange attached to a base thereof, each said recessed flange being disposed within the distal end of the hand gripping portion and fixedly retained therein.

12. A surgical instrument assembly as in claim 11, wherein the recessed flanges of the half retainer housing portions are fixedly retained therein by at least one dowel pin disposed through holes in the distal end of the hand gripping portion, and mating retaining openings in the flanges.

13. A surgical instrument assembly as in claim 12, wherein each recessed flange further comprises a shoulder adjacent the half-dome, and the distal end of the hand gripping portion comprises an end surface mating to a recessed flange shoulder to stabilize the attachment of the hand gripping portion to the shaft connecting portion of the instrument.

14. A surgical instrument assembly as in claim 13, wherein the hand gripping portion has an enlarged proximal end and the surface of the hand gripping portion comprises molded regions creating a gripping surface.

15. A surgical instrument assembly as in claim 8 wherein the instrument connector is a Hudson fitting.

16. The surgical instrument assembly of claim 8 wherein the surgical instruments is chosen from the group comprising curettes, chisels, taps and probes.

* * * * *